US00PP13714P29

(12) United States Plant Patent
Hofmann

(10) Patent No.: US PP13,714 P2
(45) Date of Patent: Apr. 8, 2003

(54) NEW GUINEA IMPATIENS PLANT NAMED 'FISIMP 131'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/080,597

(22) Filed: Feb. 22, 2002

(51) Int. Cl.[7] ..... A01H 5/00
(52) U.S. Cl. ..... Plt./318

(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisimp 131', characterized by its outwardly spreading, rounded and uniformly mounded plant habit; freely branching and freely flowering habit; large rounded dark pink-colored flowers that are positioned above and beyond the foliage; and medium green-colored leaves.

1 Drawing Sheet

BOTANICAL CLASSIFICATION/CULTIVAR DESIGNATION

*Impatiens hawkeri* cultivar Fisimp 131.

BACKGROUND OF THE INVENTION

The present Invention relates to a new and distinct cultivar of New Guinea Impatiens plant, botanically known as *Impatiens hawkeri*, and hereinafter referred to by the name 'Fisimp 131'.

The new Impatiens is a product of a planned breeding program conducted by the Inventor in Hillscheid, Germany. The objective of the breeding program is to develop new moderately compact Impatiens cultivars that flower relatively early with large rounded flowers and attractive flower colors.

The new Impatiens originated from a cross made by the Inventor in July, 1997 of the *Impatiens hawkeri* cultivar BSR-195 Salmon, disclosed in U.S. Plant Pat. No. 8,870, as the female, or seed, parent with the *Impatiens hawkeri* cultivar Riviera Hot Rose, not patented, as the male, or pollen, parent. The cultivar Fisimp 131 was discovered and selected by the Inventor as a flowering plant within the progeny of the stated cross in a controlled environment in Moncarapacho, Portugal in March, 1998.

Asexual reproduction of the new cultivar by terminal cuttings taken in Moncarapacho, Portugal, since March, 1998, has shown that the unique features of this new Impatiens are stable and reproduced true to type in successive generations.

SUMMARY OF THE INVENTION

The following traits have been repeatedly observed and are determined to be the unique characteristics of 'Fisimp 131'. These characteristics in combination distinguish 'Fisimp 131' as a new and distinct Impatiens cultivar:

1. Outwardly spreading, rounded and uniformly mounded plant habit.
2. Freely branching and freely flowering habit.
3. Large rounded dark pink-colored flowers that are positioned above and beyond the foliage.
4. Medium green-colored leaves.

Plants of the new Impatiens can be compared to plants of the female parent, the cultivar BSR-195 Salmon. In side-by-side comparisons conducted by the Inventor in Hillscheid, Germany, plants of the new Impatiens differed from plants of the cultivar BSR-195 Salmon in the following characteristics:

1. Plants of the new Impatiens were more compact than plants of the cultivar BSR-195 Salmon.
2. Leaves of plants of the new Impatiens were solid green in color whereas leaves of plants of the cultivar BSR-195 Salmon were occasionally variegated.
3. Lateral branches of plants of the new Impatiens were light green in color whereas lateral branches of plants of the cultivar BSR-195 Salmon were light red in color.
4. Flower color of plants of the new Impatiens was dark pink whereas flower color of plants of the cultivar BSR-195 Salmon was light red.

Plants of the new Impatiens can be compared to plants of the male parent, the cultivar Riviera Hot Rose. In side-by-side comparisons conducted by the Inventor in Hillscheid, Germany, plants of the new Impatiens differed from plants of the cultivar Riviera Hot Rose in the following characteristics:

1. Plants of the new Impatiens were more compact than plants of the cultivar Riviera Hot Rose.
2. Flower color of plants of the new Impatiens was lighter pink than flower color of plants of the cultivar Riviera Hot Rose.

Plants of the new Impatiens can also be compared to plants of the cultivar Danharpch, disclosed in U.S. Plant Pat. No. 12,091. In side-by-side comparisons conducted by the Inventor in Hillscheid, Germany, plants of the new Impatiens differed from plants of the cultivar Deanharpch in the following characteristics:

1. Plants of the new Impatiens were more broad and more freely branching than plants of the cultivar Danharpch.
2. Leaves of plants of the new Impatiens were shorter and more broad than leaves of plants of the cultivar Danharpch.
3. Flowers of plants of the new Impatiens were more rounded and flatter than flowers of plants of the cultivar Danharpch.
4. Flower spurs of plants of the new Impatiens were lighter pink in color than flower spurs of plants of the cultivar Danharpch.
5. Flowers of plants of the new Impatiens were darker pink in color than flowers of plants of the cultivar Danharpch.

6. Peduncles of plants of the new Impatiens were green in color whereas peduncles of plants of the cultivar Danharpch were reddish brown in color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors in the detailed botanical description which accurately describe the colors of the new Impatiens. The photograph comprises a side perspective view of a typical flowering plant of 'Fisimp 131 ' grown in a container.

DETAILED BOTANICAL DESCRIPTION

The cultivar Fisimp 131has not been observed under all possible environmental conditions. The phenotype may vary somewhat with variations in environment such as temperature and light intensity, without, however, any variance in genotype.

The aforementioned photographs, following observations and measurements describe plants grown in Langley, British Columbia, Canada, under commercial practice in a greenhouse. Rooted young plants were planted in 17.5-cm containers during the spring and the aforementioned photograph and following observations and measurements were taken during the summer about 17 weeks later. During the production of the plants, day temperatures ranged from 21 to 24° C. and night temperatures were about 17 to 18° C. In the following description, color references are made to The Royal Horticultural Society Colour Chart, 1995 Edition, except where general terms of ordinary dictionary significance are used.

Botanical classification: *Impatiens hawkeri* cultivar Fisimp 131.

Parentage:

*Female parent.*—*Impatiens hawkeri* cultivar BSR-195 Salmon, disclosed in U.S. Plant Pat. No. 8,870.

*Male parent.*—*Impatiens hawkeri* cultivar Riviera Hot Rose, not patent.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 158D in color.

Plant description:

*General appearance.*—Outwardly spreading, low, rounded and uniformly mounded plant growth habit; freely branching habit, dense and bushy appearance; freely flowering. Moderately vigorous to vigorous.

*Crop time.*—From a rooted cutting, about 10 to 11 weeks are required to produce finished flowering plants in 12-cm containers.

*Plant height.*—About 21.6 cm.

*Plant diameter or spread.*—About 54.4 cm.

*Lateral branches.*—Quantity per plant: About 14. Length: About 20 cm. Diameter: About 8 mm. Internode length: About 4.5 cm. Color: 144A to 144B.

*Foliage description.*—Arrangement: Primarily in whorls. Length: About 14 cm. Width: About 5 cm. Shape: Elliptic. Apex: Acuminate. Base: Acute. Margin: Serrulate with ciliation. Texture: Smooth, slightly rugose; glabrous. Color: Young and fully expanded foliage, upper surface: 137A to 137B. Young and fully expanded foliage, lower surface: 139C. Venation, upper surface: 145B; towards the base, slight anthocyanin, 39C, may be present. Venation, lower surface: 145B to 145C. Petiole: Length: About 2.75 cm. Diameter: About 3.5 mm. Color, upper and lower surfaces: 145B, with faint anthocyanin, 39C.

Flower description:

*Flower type and flowering habit.*—Single; large rounded dark pink-colored flowers. Freely and continuously flowering; usually about 7 to 9 flowers and flower buds per lateral branch. Flowers flat and positioned above and beyond the foliage and typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 weeks after planting.

*Flower buds.*—Length: About 2.1 cm. Diameter: About 1.5 cm. Shape: Ovoid. Color: 51B.

*Flower length.*—About 7.1 cm.

*Flower width.*—About 6.9 cm.

*Flower depth.*—About 7.5 mm.

*Petals.*—Quantity: Five per flower, imbricate. Length: Banner petals: About 3.1 cm. Lateral and base petals: About 3.2 cm. Width: Banner petal: About 4.8 cm. Lateral and base petals: About 4.3 cm. Shape: Roughly cordate. Apex: Retuse to emarginate; two shallow lobes. Base: Attenuate. Margin: Entire. Aspect: Mostly flat. Texture: Smooth; satiny. Color: When opening, upper surface: 52A. When opening, lower surface: 54B to 55A. Fully opened, upper surface: Between 52A and 52B; towards base or small eye, 55B. With subsequent development, color fading slightly to 52B. Fully opened, lower surface: 54B to 55A.

*Spur.*—Quantity: One per flower. Length: About 6.1 cm. Diameter: At apex: About 0.5 mm. At flower: About 3 mm. Aspect: Curved. Color: 50B to 50C.

*Peduncles.*—Length: About 4 cm. Diameter: About 2 mm. Strength: Strong, flexible. Angle: About 45° from the lateral branch. Color: 144C.

*Reproductive organs.*—Androecium: Stamen number: Five fused at anthers, hooded; filaments free. Anther length: About 6 mm. Anther shape: Obovate. Anther color: 52C. Pollen amount: Moderate. Pollen color: 8D. Gynoecium: Pistil quantity: One per flower. Pistil length: About 4.5 mm. Stigma color: 18D. Style color: Close to 18D. Ovary: Five-celled. Ovary color: Initially 143B, then with development, 137D.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisimp 131', as illustrated and described.

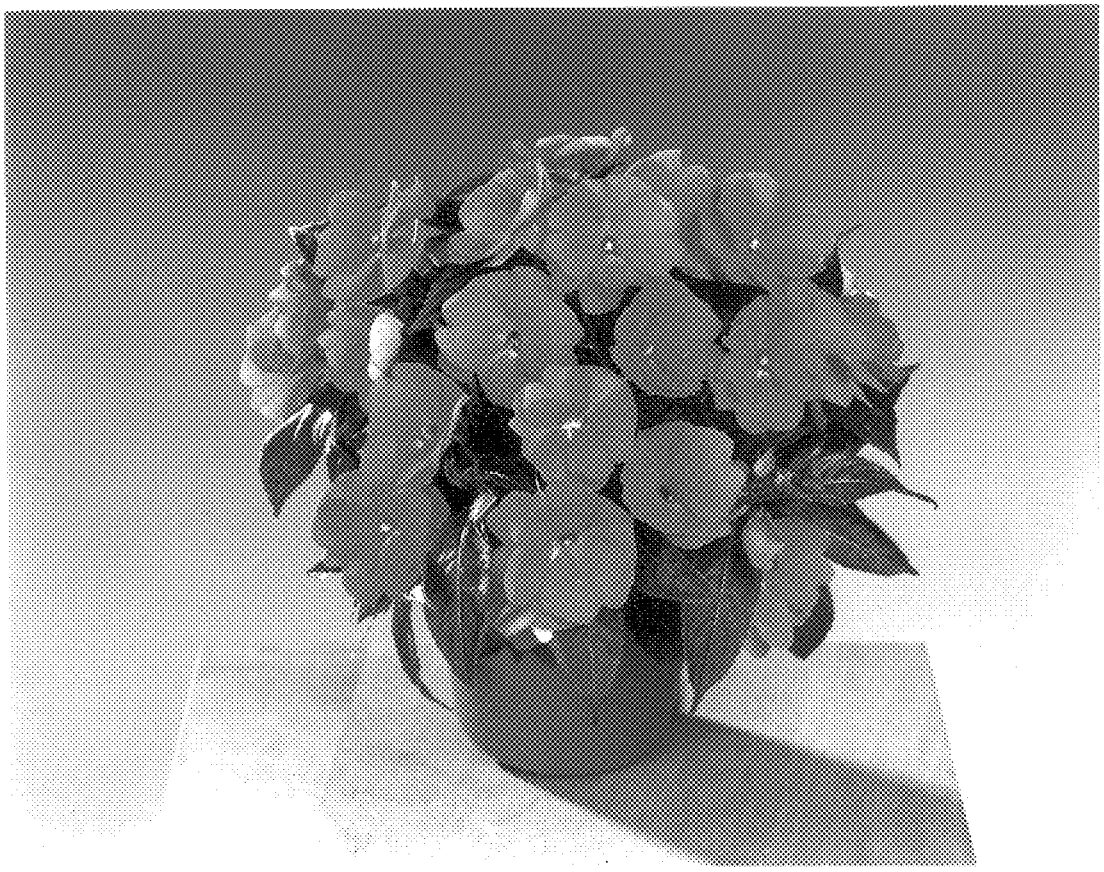

* * * * *